(12) United States Patent
Miyauchi

(10) Patent No.: US 6,612,189 B1
(45) Date of Patent: Sep. 2, 2003

(54) TENSILE TESTING MACHINE FOR VARIOUSLY CROSS SECTIONAL MATERIALS

(75) Inventor: Kunio Miyauchi, Tokyo (JP)

(73) Assignee: WE Plan Company, Tokyo (JP)

( * ) Notice: Subject to any disclaimer, the term of this patent is extended or adjusted under 35 U.S.C. 154(b) by 0 days.

(21) Appl. No.: 09/392,482

(22) Filed: Sep. 9, 1999

(30) Foreign Application Priority Data

Sep. 9, 1998 (JP) .......................................... 10-254828

(51) Int. Cl.[7] ................................................ G01L 1/26
(52) U.S. Cl. .................. 73/862.392; 73/829; 73/862.55
(58) Field of Search ........................ 73/826, 831, 103, 73/829, 837, 159, 789, 862.392, 862.55

(56) References Cited

U.S. PATENT DOCUMENTS

| | | | |
|---|---|---|---|
| 3,916,681 A | * 11/1975 | Ryckman et al. | ............. 73/103 |
| 3,927,558 A | * 12/1975 | Philippe et al. | ................ 73/95 |
| 4,299,129 A | * 11/1981 | Ritzinger | ..................... 73/746 |
| 4,404,840 A | * 9/1983 | Burr et al. | ........................ 73/7 |
| 5,437,182 A | 8/1995 | Plaschy et al. | ............... 73/160 |
| 5,948,994 A | * 9/1999 | Jen et al. | ...................... 73/856 |
| 6,041,660 A | * 3/2000 | Fujitaka et al. | .............. 73/826 |

FOREIGN PATENT DOCUMENTS

| | | |
|---|---|---|
| EP | 0 403 988 A2 | 6/1990 |
| JP | 60-033030 | 2/1985 |
| JP | 61-237037 | 10/1986 |

OTHER PUBLICATIONS

Patent Abstracts of Japan, Publication No.: 07055670, Publication Date: Mar. 3, 1995.
Patent Abstracts of Japan, Publication No.: 56019433, Publication Date: Feb. 24, 1981.
Patent Abstracts of Japan, Publication No.: 02120640, Publication Date: May 8, 1990.

* cited by examiner

*Primary Examiner*—Harshad Patel
(74) *Attorney, Agent, or Firm*—Birch, Stewart, Kolasch & Birch, LLP

(57) ABSTRACT

In order to provide a tensile testing machine of variously cross-sectioned materials which has a very concise structure to make possible more accurate measurement of tensile force, the testing machine is equipped with two roll stands which have gripping rolls available gripping variously cross-sectioned specimens. One or both of the roll stands are hanging. The machine is also equipped with a device for giving a certain initial load to the load cells placed between the roll stands, if necessary.

14 Claims, 8 Drawing Sheets

TENSILE TESTING MACHINE FOR VARIOUSLY CROSS SECTIONAL MATERIALS

BACKGROUND OF THE INVENTION

1. Field of the Invention

The present invention relates to the tensile testing machine of variously cross-sectioned materials, and in particular for tensile testing of such variously cross-sectioned materials as sheets, wires, rods and pipes.

2. Description of the Related Art

The present inventor developed a new method and machine for tensile test of sheet materials as described in Japanese Patent Publication No. 3-47448 (1991-47448) and Japanese Patent Publication No. 4-31053 (1992-31053).

According to this method, a test specimen is gripped by each pair of rolls respectively at each end of a specimen, these rolls are rotated at the standing positions in the direction reverse to each other to stretch out the specimen so that the point of non-displacement appears at the center of specimen with the same rotating speed of all the rolls. The constant strain rate test is performed easily by using parallel-shaped straight specimens where it is possible to realize the continuous microscopic observation of such mechanical properties of sheet materials as deformation of crystal grains and slip pattern during plastic deformation.

In the tensile test of the above-described machine, however, there was an unfavorable problem in the measurement of tensile load caused by a fairly big friction between the rail and the movable roll stand on the rail.

It is necessary to solve new various technical problems for more accurate measurement of tensile force.

Further it is also necessary to develop a quite new system very different from the automated one in the traditional tensile testing machines, for full automation of tensile test.

OBJECTS AND SUMMARY OF THE INVENTION

From the above described point of views, the present invention aims at the development of a tensile testing machine of variously cross-sectioned materials which is of concise construction and make possible more accurate measurement of tensile properties.

Another object of the present invention is to provide a fully automated tensile testing machine of variously cross-sectioned materials.

For achievement of the above-described objects, the tensile testing machine of variously cross-sectioned materials according to the present invention is characterized by hanging at least one of the roll stands in which a test specimen is gripped and elongated by the rotation of gripping rolls and is also characterized by successfully removing the outer effect on the measurement of tensile force.

The present unique automated system is benefited by the features of the present testing method, to make possible a very high efficient rate of feed-in and feed-out system and simultaneous measurement of various tensile properties.

The tensile testing machine equipped with various functions as described above according to the present invention is available for assuring high efficiency, low energy consumption and high reliability in simultaneous measurement of tensile force, work hardening index n, normal anisotropy ratio r and the other tensile properties in fully automated continuous and long time tensile test of sheet materials.

The invention is characterized by freely hanging one or both of the roll stands which have the gripping rolls for a variously cross-sectioned test specimen and, if necessary, is equipped with a device to give a certain initial load to load cells placed between the two roll stands before the start of tensile test.

In the invention, a cleaning device for keeping the optimal surface of gripping rolls by brushing during the operation of tensile test can be provided.

It is impossible to brush the gripping surface during tensile test in the traditional tensile testing machine, while the present invention makes it possible to clean the surface of gripping rolls with brushes simultaneously during tensile test.

The invention provides an extensometer, which has two probes lightly touching respectively to the end points of gauge length for measurement of elongation in tensile.

The invention provides another extensometer, which has two small rolls touching respectively to the end points of gauge length, keeping the initial distance between the rolls and measuring the elongation of a specimen with the rotation of the two rolls.

The invention also provides gripping rolls which have uneven surface profiles striped in the axial direction of rolls or in symmetrical inclination to the axial direction. Two or more uneven surface profiles in the circumferential direction and a constant diameter with the gripping range or small crown in the invention are provided.

The invention further provides a measuring device of specimen width or thickness touching two small rolls to the specimen and detecting the position of a supporting point in the center of two rolls as the average value between the touched points of two rolls.

The invention additionally provides cartridges for containing specimens, feed-in device of specimen from the cartridge, measuring devices of specimen width and thickness before the start of test and an extensometer for measuring the elongation of specimen.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbefore and the accompanying drawings which are given by way of illustration only, and thus are not limitative of the present invention, and wherein.

DETAILED DESCRIPTION OF THE PREFERRED EMBODIMENTS

One example of actual performances of the tensile testing machine according to he present invention is explained below in detail with respect to the attached drawings.

Figure 1B:
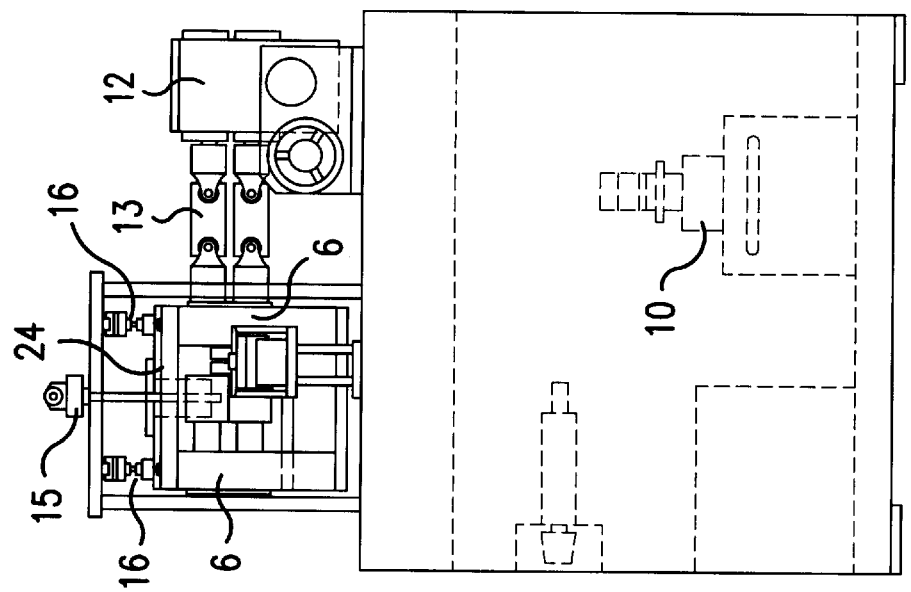
FIG. 1(*a*) is the structural outline of the tensile testing machine of variously cross-sectioned materials in front view according to the present invention, and FIG. 1(*b*) is the structural outline of variously cross-sectioned materials in right-side view according to the present invention.
Figure 1A:
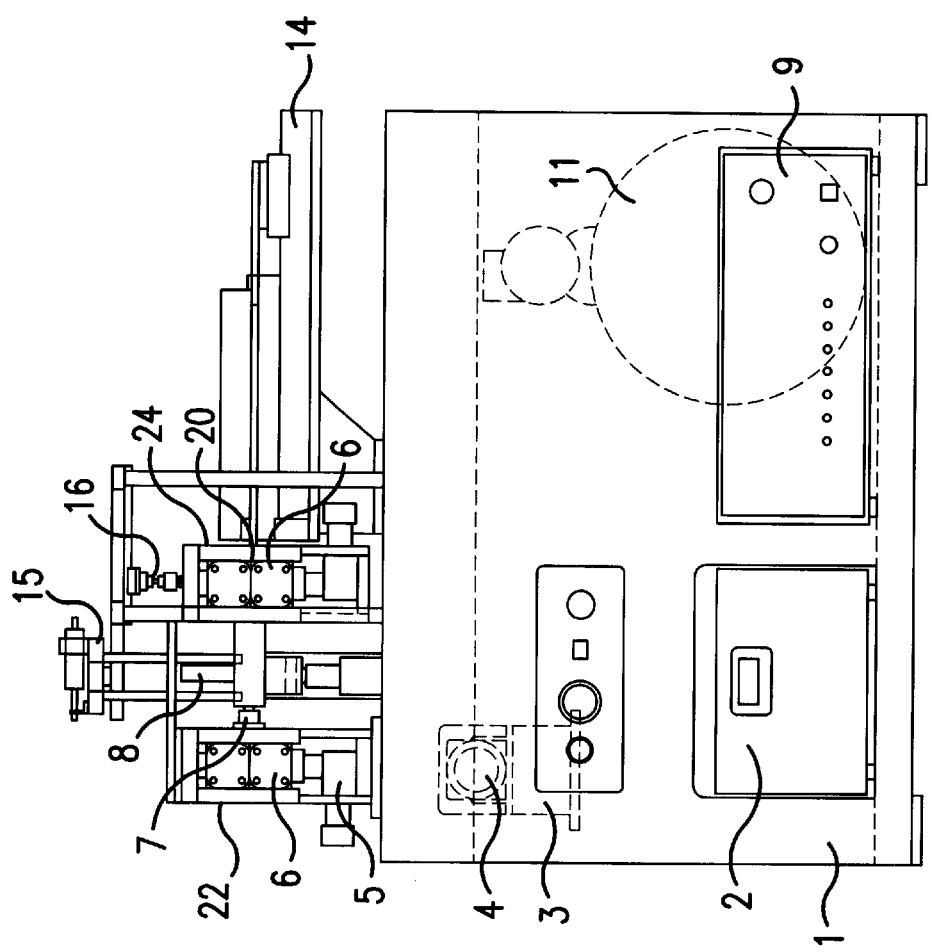

FIG. 1(a) is front view of the tensile testing machine of variously cross-sectioned materials according to the present invention and FIG. 1(b) is the right-side view of the same machine.

Figure 2:
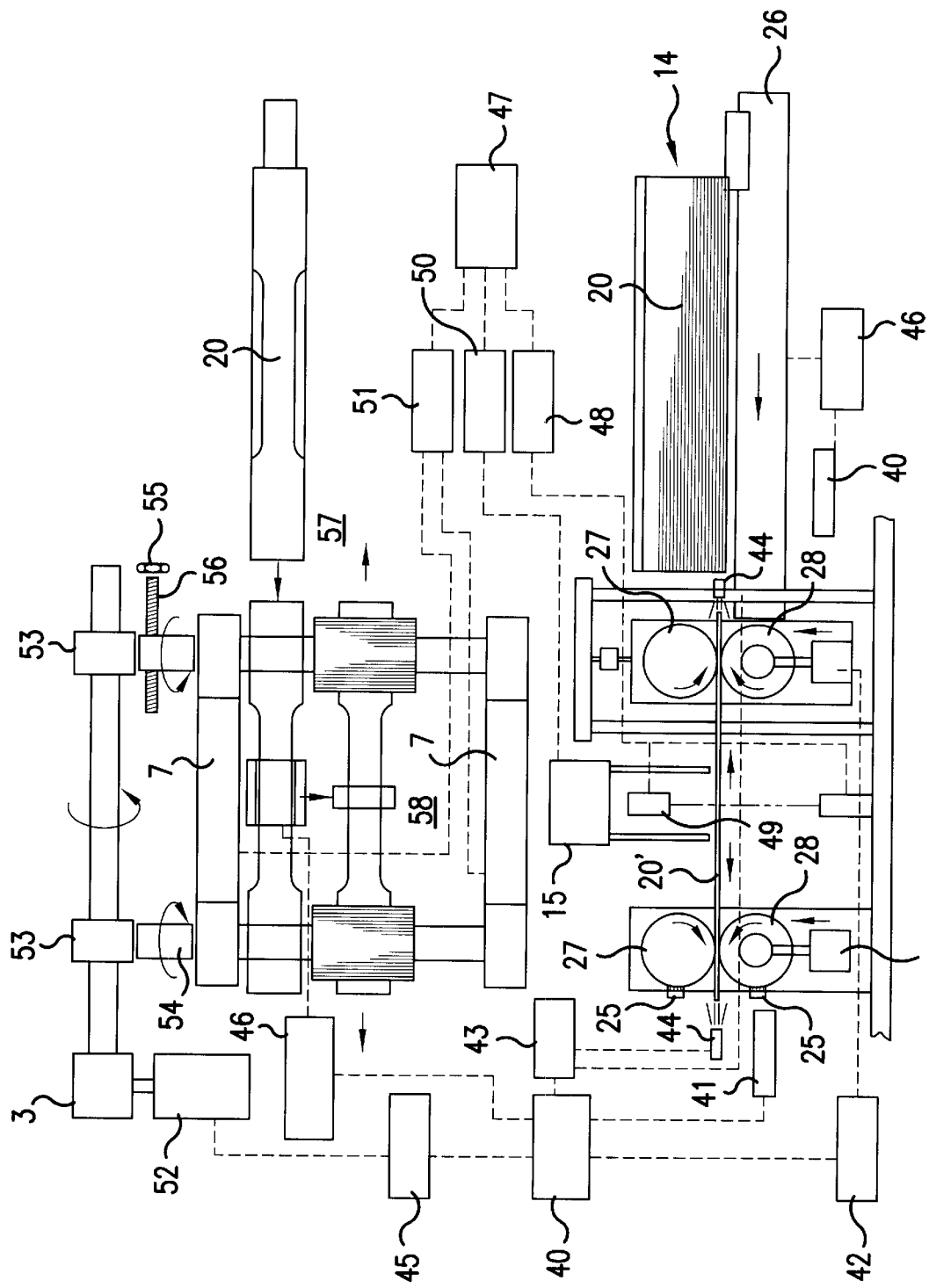
FIG. 2 is an example of the conceptual diagram of actual performance in the test, where the upper part corresponds to the outline of the main part in horizontal cross-section in FIG. 1(*a*) and the lower part shows the outline of the main part in vertical cross-section in FIG. 1(*b*)

FIG. 2 is to give an illustration, which explains an example of actual testing process. The horizontal cross-section of main parts in FIG. 1(a) is shown in the upper part of FIG. 2, while the vertical cross-section of main parts in FIG. 1(b) is in the lower part of FIG. 2.

The main testing part in the tensile testing machine of variously cross-sectioned materials is placed on the rack 1.

The main part of the testing machine includes two roll stands 22 and 24 containing the rotary grips 6 of a pair of upper and lower rolls 27, 28 for gripping and stretching a specimen 20, two rods of load cell 7 installed between the two roll stands 22 and 24 for measuring the load, a width measuring device 8, an extensometer 15, oil cylinders for gripping the specimen 20, free joints 16 hanging the roll stand 24, a specimen cartridge 14 before the test, universal joints 13 transmitting the torque to the gripping rolls, and a gear box 12 regulating the rotating speed. A P.C. 47 for data processing is connected to the extensometer 15. This P.C. 47 is also connected to an amplifier 48 for laser sensor 49; to an amplifier 50 for the extensometer 15; and to an amplifier 51 for load cell 7. The speed control motor driver 45 is connected to the speed control motor 52 which is connected to reduction gear 3. This gear 3 has a plurality of gear boxes 53 connected to ball joints 54. A manual handle 55 is also provided for feed screw 56 for gear box adjustment. In FIG. 2, a first stage 57 and third stage 58 are shown.

In the rack 1, an electric motor 4 for rotating the rolls, a compressor 11 and an oil pressure unit 10 to increase the oil pressure in the oil cylinder 5 and raise the lower roll for gripping the specimen 20, a control box 9 for testing operation, and a scrap box 2 for tested specimens are installed.

The brushes 25 are prepared touching the roll surface 27, 28 and gives brushing onto the roll surface with the rotation of rolls as seen in FIG. 6. A P.C. control 40 is connected to brush 25 through a digital controller 41 for the cylinder. This P.C. control 40 is also connected to a digital control 42 for the oil pressure cylinder 5 and to an air digital controller 43 for blowers 44 adjacent ends of the specimen 20. The P.C. 40 is also connected to a speed control motor driver 45 and a cylinder digital controller 46.

As explained above, FIG. 2 illustrates the outline of actual performance in the testing process, while the upper part of FIG. 2 shows the outline of main part in horizontal cross-section in FIG. 1(a) and the lower part of FIG. 2 shows the outline of main part in vertical cross-section in FIG. 1(b).

In FIG. 2, a specimen 20' at the lowest position in the specimen cartridge 14 on the right side is fed out in the longitudinal direction by a cylinder 26 for the pushing out of the specimen to the waiting position for a next test which is positioned just beside the two gripping rolls 27, 28.

Figure 4:
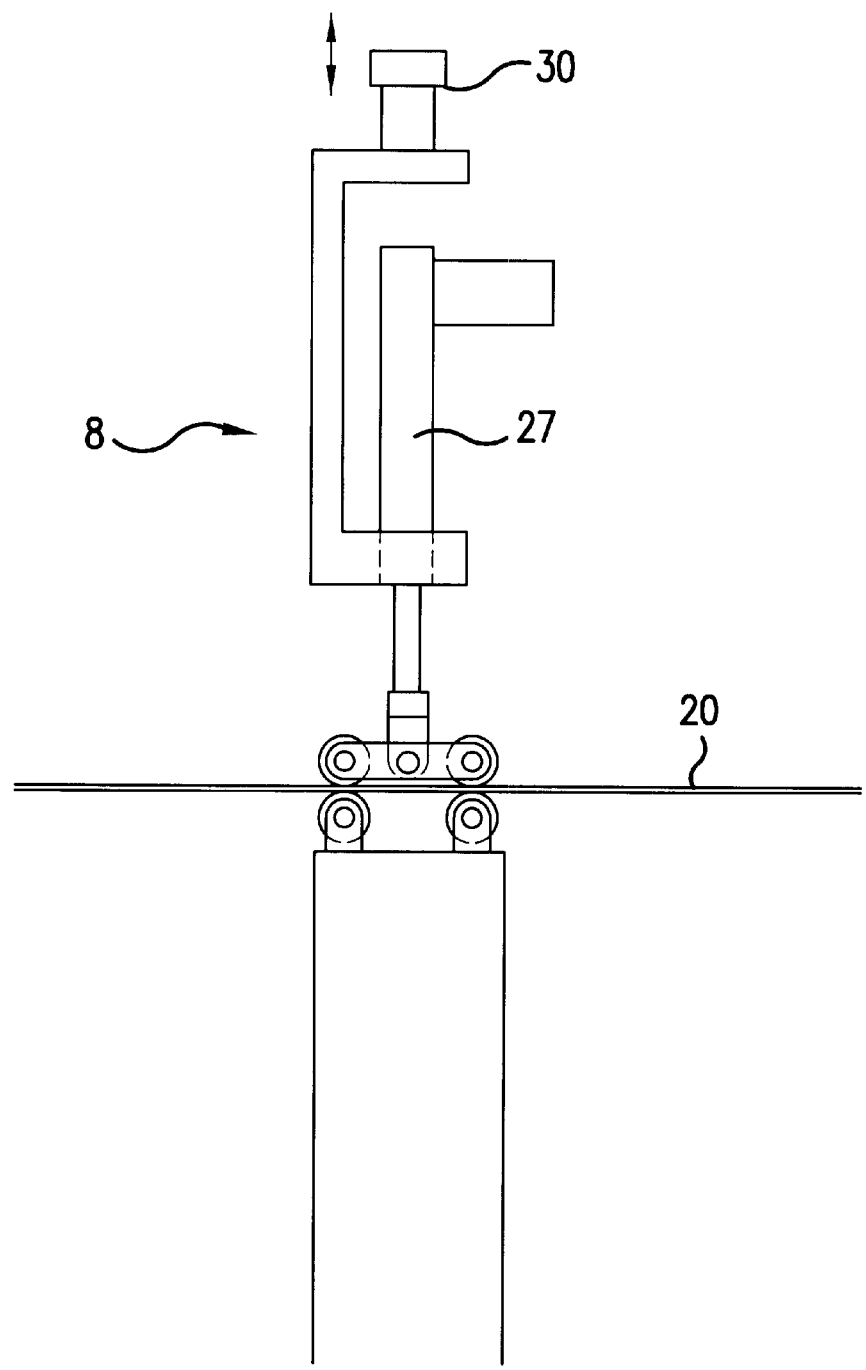
FIG. 4 illustrates a device for measuring the specimen thickness.

The specimen thickness is automatically measured by such a device 8 as shown in FIG. 4, while the specimen undergoes the above-described movement. The width measuring device 8 includes a magnetic scale 27 and an air cylinder drive 30.

Next, the waiting specimen is laterally moved to the testing position, the width measurement 8 is done by using a width measuring device of the same system as described in FIG. 4 or by using an optical device for width measurement, and the elongation is detected by touching the probes of an extensometer 15 softly onto the surface of the specimen during tensile test.

The next specimen is fed from the specimen cartridge 14 synchronously with the start of testing and it waits for the next test, to be subjected repeatedly to the same process as described above.

When the specimen is fractured at the limit of elongation, the fractured pieces are fed out of the gripping rolls 27, 28 and are received in the lower scrap box 2.

The lower gripping rolls 28 begin to descend immediately by the oil pressure cylinder 5 after fracture occurs. Then, the next specimen is moved to the testing position and is tested in the same manner as described above.

Figure 3:
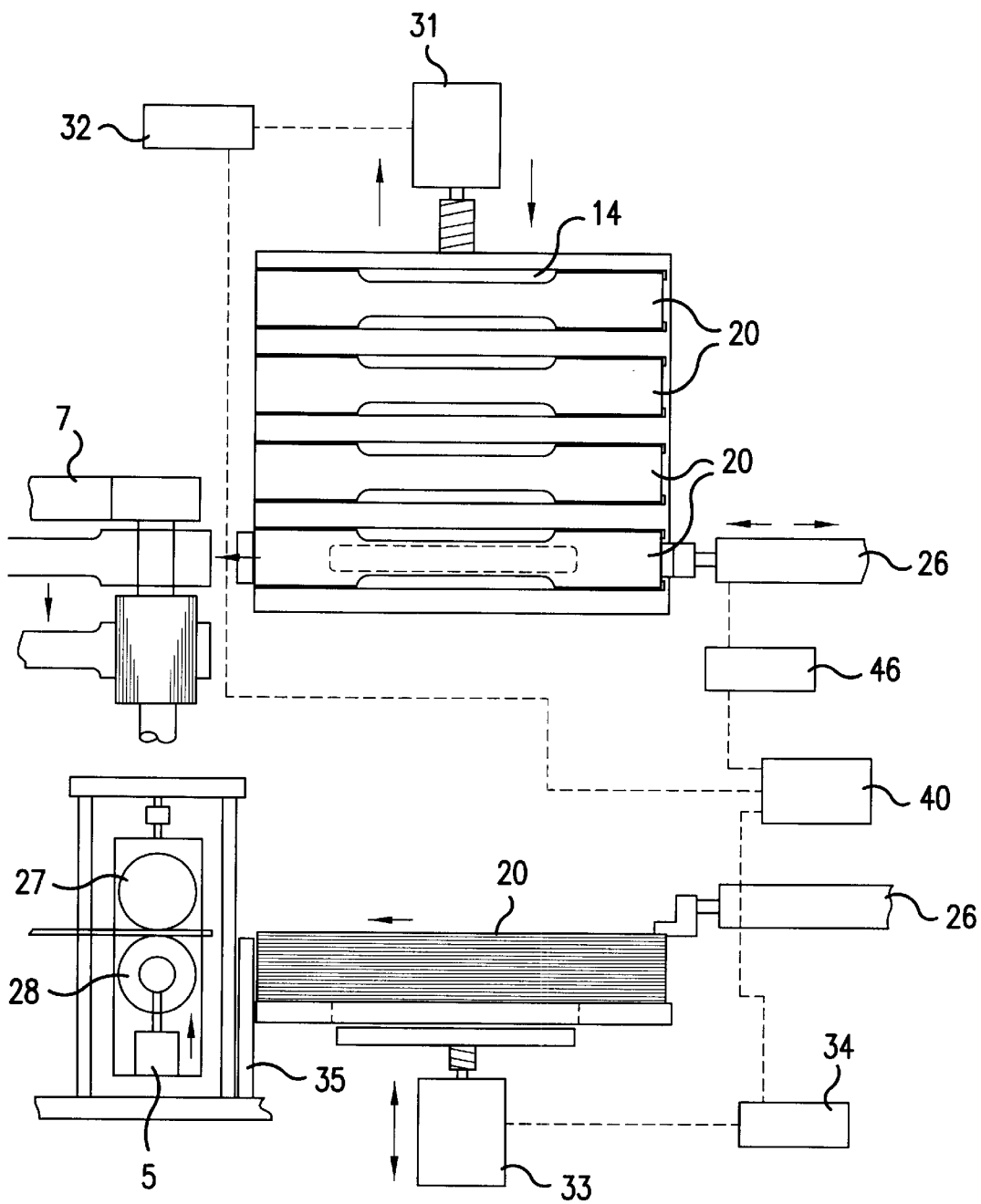
FIG. 3 is an illustrative diagram of the fully automated continuous tensile test for a long time.

FIG. 3 shows an example of automated specimen feeder for tensile test for a long time. As many cartridges 14 as necessary are set in a row as shown in the upper part of FIG. 3. When the cartridge 14 becomes empty, it is fed out and the next cartridge is fed in, to make possible the fully automated continuous tensile test for a long time. A reversible motor 31 connected to reversible motor driver 32 moves the specimen cartridges.

The push-out system of specimens from the cartridge using cylinder 26 in FIG. 3 is an example of pushing out the top specimen in the cartridge. A stepping motor 33 with a driver 34 is provided for elevating the specimen 20. A specimen step 35 is also provided on the downstream side of the specimen 20.

An example of the thickness measuring device is shown in FIG. 4, where miniature bearings are used for the rotating center. The measurement of thickness can be done at many points as well as all over the test range while the specimen 20 is moving from the cartridge to the waiting position.

The present device detects the thickness at two points at the same time and averages the two values. In this method, the number of measurement is substantially doubled, to result in a doubled reliability of measurement.

Figure 5B:
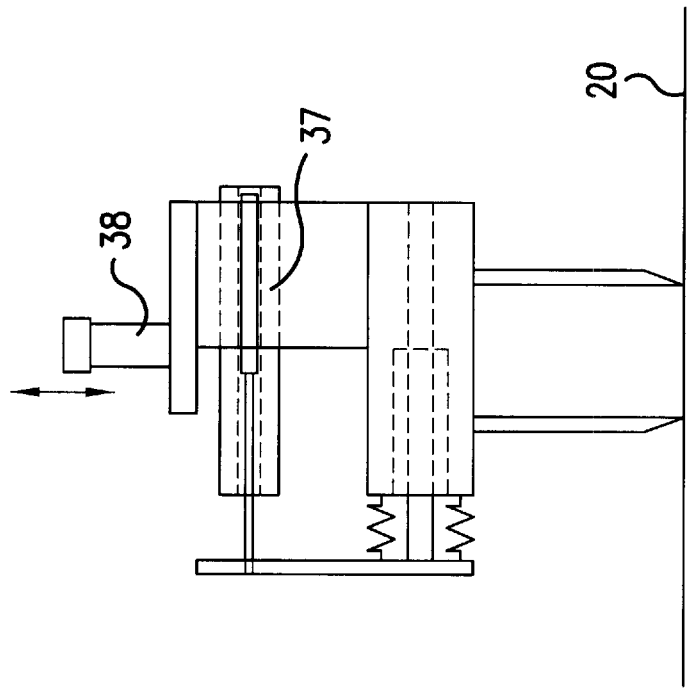
FIG. 5 illustrates a schematic diagram of mechanical devices for measuring the elongation of a specimen, where (a) is for using the magnetic scale and (b) is for using the differential transformer.
Figure 5A:
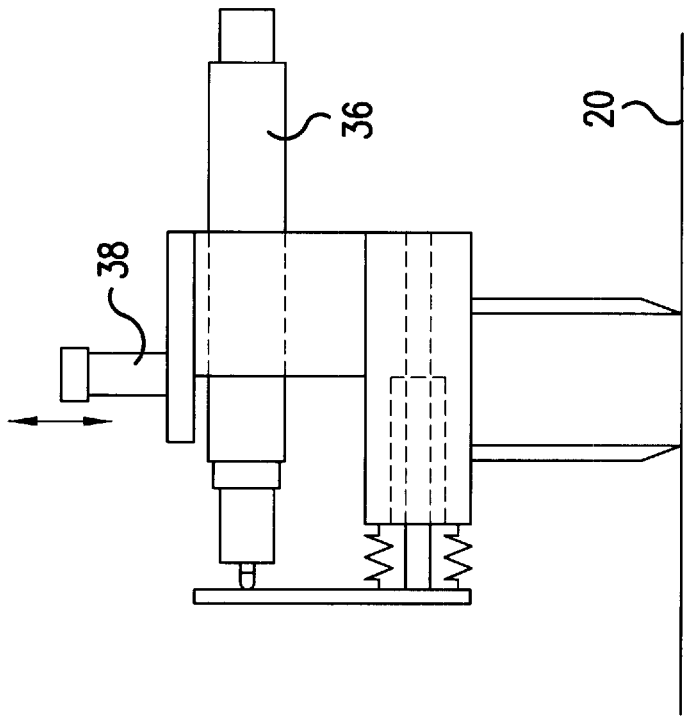

FIGS. 5(a) and 5(b) illustrate mechanical measuring devices of elongation FIG. 5(a) uses a magnetic scale 36 and FIG. 5(b) uses a differential transformer 37. An air cylinder drive 38 is provided for either measuring device.

There is no substantial difference in accuracy and reliability between the magnetic scale 36 and the differential transformer 37. The light touch of probes onto the specimen surface can sharply detect the elongation of a specimen without causing any unfavorable effect on the true deforming behavior of test material, to obtain the tensile properties of material with high reliability.

Figure 6A:
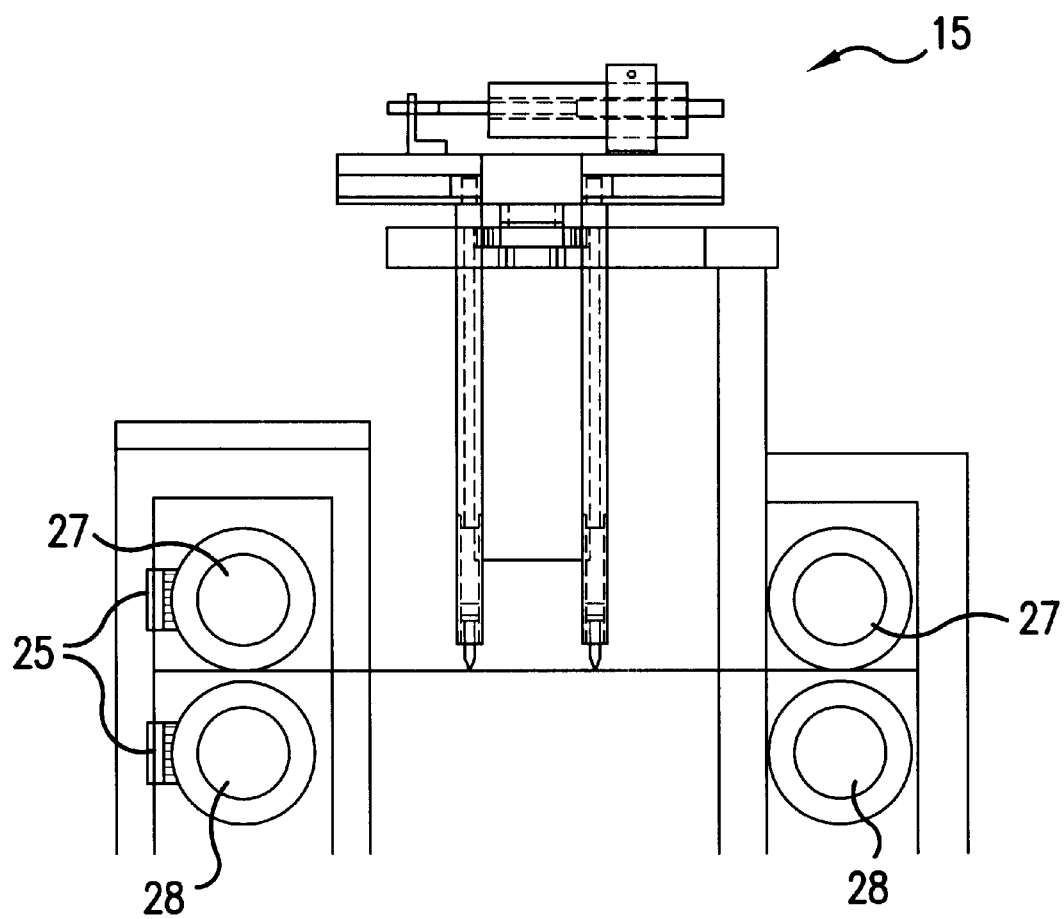
FIG. 6(a) shows a side view and FIG. 6(b) shows a plan view of a device for measuring elongation, which has actually been produced and has proved its satisfactory detecting ability.
Figure 6B:
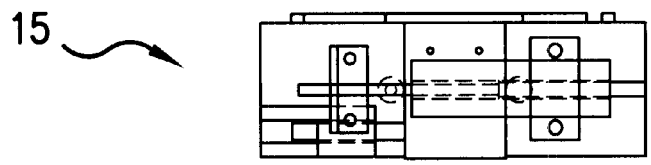

FIGS. 6(a) and 6(b) are an example of an extensometer 15 which has been actually produced and as shown a satisfactory detecting ability.

Figure 7A:
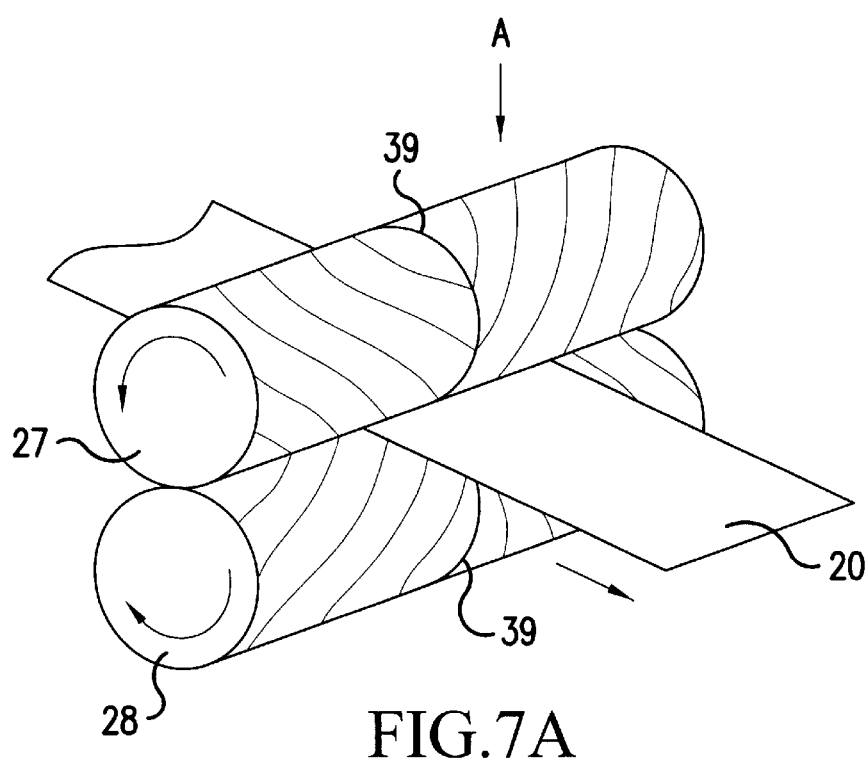
FIG. 7 shows the illustrative diagrams of gripping roll, where (a) is the perspective view and (b) is a plan view in the direction of arrow A.
Figure 7B:
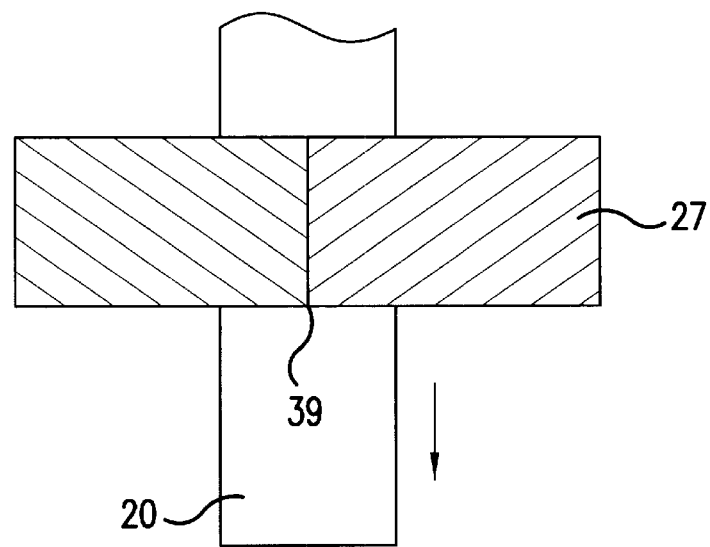

FIGS. 7(a) and 7(b) illustrate the surface of gripping rolls 27, 28. The groove and projection pattern striped in the inclined direction is symmetrical about the center line 39, so that the specimen is subjected to the component of gripping force toward the center to keep the right alignment in tensile direction and obtain higher fidelity in measurement.

Figure 8:
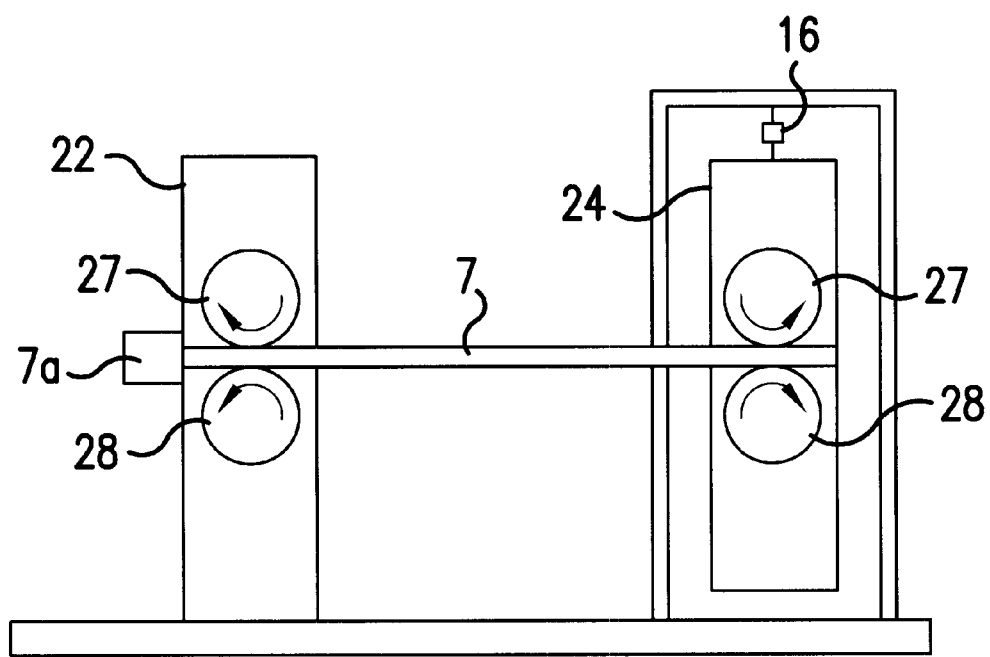
FIG 8 is a simplified conceptual diagram of part of FIG. 2.

FIG. 8 is a simplified drawing showing the arrangement of the roll stands with the load cells. Fixed roll stand 22 includes an upper roll 27 and lower roll 28 as previously described. Likewise, roll stand 24 includes upper roll 27 and lower roll 28 as well. Free joint 16 hangs roll stand 24 from a fixed framework. When the rolls move in the direction indicated by the arrows, the sample tested is pulled outwardly from each roll stand. As the rolls pull, the stands to which they are attached are pulled inwardly toward each other. The amount of force applied by the rolls can be measured by placing a load cell between the two roll stands. This can be accomplished by a pair of load cells 7 placed on opposite ends of the roll stands. FIG. 8 shows one of these load cells, with the other being hidden directly behind this cell, at the other end of the roll stands. Although one pair of load cells is shown as being mounted in the center vertically, it also would be possible to use two pairs of cells, with one pair above the level of the rollers and one below the level of the rollers. These could be mounted like load cells shown, attached across the ends of the roll stand. Alternatively, it would also be possible to place the load cells between the stands so that the facing sides bear directly on the load cell. If desired, the load cell may be equipped with a device 7a which provides an initial load to the load cell before the testing begins. With this arrangement, these stands are preloaded to hold them tightly in position before the rolls start to move, and also provide an initial output value for the load cell to make the reading more accurate. While this initial load device is shown as being connected to the end of the load cell mounted on the fixed stand, it can also mounted elsewhere or even be included within the load cell housing.

The present invention is characterized by such a concise and rational structure as so far described and consequently makes it possible to produce a tensile testing machine of variously cross-sectioned materials available for more accurate measurement of tensile force.

The present invention has such rational characteristics as so far described, to easily make possible the fully automated tensile testing machine of variously cross-sectioned materials.

It will be appreciated by those of ordinary skill in the art that the present invention can be embodied in other specific forms without departing from the spirit or essential characteristics thereof.

The presently disclosed embodiments are therefore considered in all respects to be illustrated and not restrictive. The scope of the invention is indicated by the appended claims rather than the foregoing description, and all changes that come within the meaning and range of equivalents thereof are intended to be embraced therein.

The entire disclosure of Japanese Patent Application No. 10-254828 filed on Sep. 9, 1998 including specification, claims, drawings and summary are incorporated herein by reference in its entirety.

What is claimed is:

1. A tensile testing machine for testing variously cross-sectioned specimens, comprising:

two roll stands, each of the two roll stands having a pair of oppositely rotating gripping rolls of a cross-section which corresponds to the cross-section of a specimen to be tested, the specimen being gripped between the gripping rolls so that opposite ends of said specimen are pulled in opposite directions, at least one of said roll stands being freely hanging from an overhead support;

at least one load cell placed between the two roll stands; and a device for applying a predetermined constant compressive. load to the at least one load cell placed between the two roll stands.

2. The tensile testing machine according to claim 1, further comprising a device for cleaning a surface of at least one of the gripping rolls whereby an optimal gripping condition is maintained during testing.

3. The tensile testing machine according to claim 1, further comprising an extensometer for detecting elongation of a predetermined gauge length, the extensometer having two probes which contact the specimen during tensile testing.

4. The tensile testing machine according to claim 1, further comprising an extensometer for detecting elongation of a predetermined gauge length, the extensometer contacts two rolls at ends of the specimen and measures rotation of the two rolls.

5. The tensile testing machine according to claim 1, wherein the gripping rolls each have a surface which is striped in an axial direction to form an uneven surface, the rolls having one of a same diameter and a small crown within a gripping range.

6. The tensile testing machine according to claim 1, wherein the gripping rolls each have a surface which is striped in a direction inclined to an axial direction to form an uneven surface, the rolls having one of a same diameter and a small crown within a gripping range.

7. The tensile testing machine according to claim 1, further comprising at least one measuring device for at least one of a width and thickness of the specimen, the measuring device including two rolls which contact the specimen and detect a position of a supporting point at a center of the two rolls and detect an average position of the two rolls.

8. The tensile testing machine according to claim 1, further comprising:

a plurality of cartridges for specimens to be tested;

a feed-in device for the specimen;

devices for measuring width and thickness of specimens before and during testing; and a device for measuring elongation of the specimen.

9. The tensile testing machine according to claim 1, wherein at least one of the gripping rolls is rotatable about a longitudinal axis, the longitudinal axis extending through the at least one gripping roll.

10. The tensile testing machine according to claim 9, wherein the longitudinal axis of the at least one gripping roll fails to intersect the specimen to be tested.

11. The tensile testing machine according to claim 10, wherein the longitudinal axis of the at least one gripping roll is parallel to the specimen to be tested.

12. The tensile testing machine according to claim 1, wherein a plurality of the gripping rolls are rotatable.

13. The tensile testing machine according to claim 12, wherein the rotatable gripping rolls each rotate about a respective longitudinal axis and wherein the longitudinal axes are parallel to the specimen to be tested.

14. The tensile testing machine according to claim 1, wherein the two roll stands include a first roll stand and a second roll stand, a first gripping roll of the first roll stand being a fixed distance from a first gripping roll of the second roll stand.

* * * * *